United States Patent [19]
Sutherland et al.

[11] Patent Number: 5,563,037
[45] Date of Patent: Oct. 8, 1996

[54] HOMOGENEOUS METHOD FOR ASSAY OF DOUBLE-STRANDED NUCLEIC ACIDS USING FLUORESCENT DYES AND KIT USEFUL THEREIN

[75] Inventors: John W. H. Sutherland; David R. Patterson, both of Rochester, N.Y.

[73] Assignee: Johnson & Johnson Clinical Diagnostics, Inc., Rochester, N.Y.

[21] Appl. No.: 576,861

[22] Filed: Dec. 21, 1995

Related U.S. Application Data

[63] Continuation of Ser. No. 235,396, Apr. 29, 1994, abandoned.

[51] Int. Cl.$^6$ .............................. C12Q 1/68; C12P 19/34; C07H 21/02; C12N 15/00
[52] U.S. Cl. .............................. 435/6; 435/91.2; 435/810; 536/23.1; 536/24.33; 536/25.32; 935/8; 935/76; 935/77; 935/78; 546/152; 546/176
[58] Field of Search .............................. 435/6, 91.2, 810, 435/183, 172.1; 436/109, 164, 172, 546, 94, 800; 536/23.1, 24.33, 75.32; 935/76, 77, 78, 8; 546/176, 152

[56] References Cited

U.S. PATENT DOCUMENTS

| | | | |
|---|---|---|---|
| 4,257,774 | 3/1981 | Richardson et al. | 23/230 |
| 4,544,546 | 10/1985 | Wang et al. | 424/7.1 |
| 4,777,129 | 10/1988 | Dattagupta et al. | 435/6 |
| 4,883,867 | 11/1989 | Lee et al. | 536/28 |
| 4,937,198 | 6/1990 | Lee et al. | 436/94 |
| 4,957,870 | 9/1990 | Lee et al. | 436/63 |
| 5,026,840 | 6/1991 | Dattagupta et al. | 536/27 |
| 5,047,321 | 9/1991 | Loken et al. | 435/6 |
| 5,049,490 | 9/1991 | Sutherland et al. | 435/6 |
| 5,242,797 | 9/1993 | Hirschfeld | 435/6 |
| 5,312,921 | 5/1994 | Glazer et al. | 546/108 |
| 5,321,130 | 6/1994 | Yue et al. | 536/23.1 |

FOREIGN PATENT DOCUMENTS

| | | | |
|---|---|---|---|
| 0443823A1 | 8/1991 | European Pat. Off. | C12Q 1/48 |
| 0487218A1 | 5/1992 | European Pat. Off. | C12Q 1/68 |
| 0512334A2 | 11/1992 | European Pat. Off. | C12Q 1/68 |
| 512334 | 11/1992 | European Pat. Off. | C12Q 1/68 |
| 05040097A | 2/1993 | Japan | G01N 21/78 |
| 2074340A | 10/1981 | United Kingdom | G01N 33/48 |
| 9113897A | 3/1991 | WIPO . | |
| WO91/13897 | 9/1991 | WIPO | C02H 15/12 |
| 93/04077 | 3/1993 | WIPO | C07H 15/26 |
| 93/06482 | 4/1993 | WIPO | G01N 33/48 |

OTHER PUBLICATIONS

Scott C. Benson et al., Heterodimeric DNA–Binding Dyes Designed For Energey Transfer: Stability And Applications Of The DNA Complexes, 5720–5726 Nucleic Acids Research, 1993, vol. 21, No. 24.

Scott C. Benson et al., Heterodimeric DNA–Binding Dyes Designed For Energy Transfer: Synethesis And Spectroscopic Properties, 5727–5735 Nucleic Acids Research, 1993, vol. 21, No. 24.

Mansfield et al, *BioTechniques*, 15(2), pp. 274–279 (1993).

Gaugain et al, *Biochemistry*, 17(24), pp. 5078–5088 (1978).

Benson et al, *Nucl. Acids Res.*,21(24), pp. 5720–5726 (1993).

Benson et al, *Nucl. Acids Res.*, 21(24), pp. 5727–5735 (1993).

Rye et al, *Nucl. Acids Res.*, 20(11), pp. 2803–2812 (1992).

"BioProbes 18", by Molecular Probes, Inc., Nov., 1993.

(List continued on next page.)

*Primary Examiner*—W. Gary Jones
*Assistant Examiner*—Bradley L. Sisson

[57] ABSTRACT

A highly sensitive homogeneous assay allows for quantitative detection of amplified nucleic acids. This detection is achieved during or after amplification with a high affinity fluorescent dye which is from the class of unsymmetrical cyanine dyes having at least two positive charges and a binding constant ($K_b$) within the range of from about $1 \times 10^4$ to about $5 \times 10^5$ (molar$^{-1}$). The reagents used for the assay can be contained in a kit designed for amplification such as by polymerase chain reaction.

19 Claims, 1 Drawing Sheet

OTHER PUBLICATIONS

Haugland, *Handbook of Fluorescent Probes & Research Chemicals*, 5th Ed., 1992–1994, pp. 221–229.

Johnson et al, Poster #1806 presented at 1992 Biophysical Society/ASBMB Joint Mtg., Houston, TX.

Higuchi et al, *BioTechnology*, Vo. 10, pp. 413–417, 1992.

Glazer et al, *Nature*, vol. 359, pp. 859–861, 1992.

Daxhelet et al, *Anal. Biochem.*, 179, pp. 401–403 (1989).

Lee et al, *Cytometry*, 7, pp. 508–517 (1986).

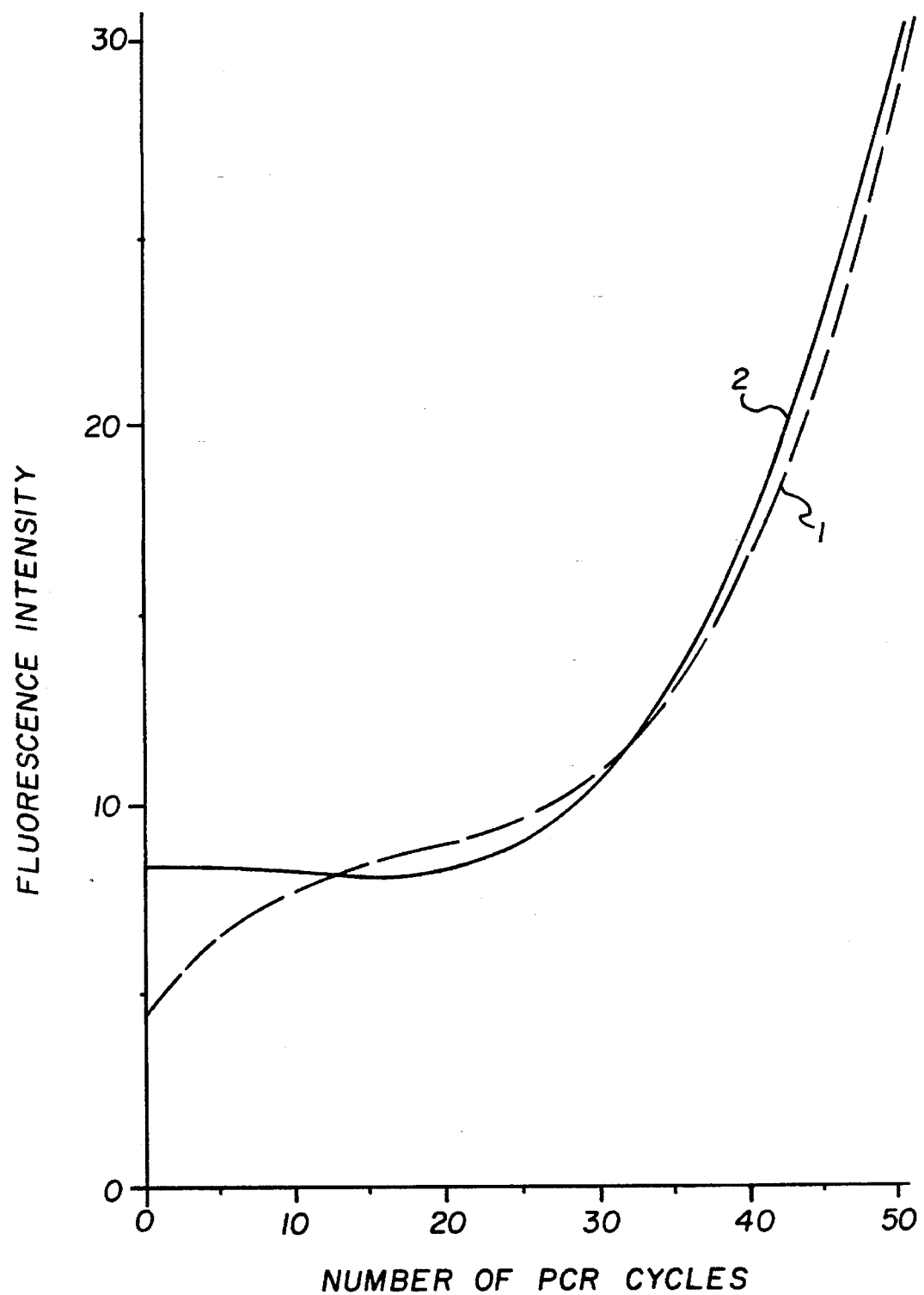

HOMOGENEOUS METHOD FOR ASSAY OF DOUBLE-STRANDED NUCLEIC ACIDS USING FLUORESCENT DYES AND KIT USEFUL THEREIN

This is a continuation of application Ser. No. 08/235,396, filed Apr. 29, 1994, now abandoned.

FIELD OF THE INVENTION

This invention relates to a homogeneous assay for the detection of target double-stranded nucleic acids. Such an assay has use in various diagnostic, investigative and research procedures, and particularly in the detection of infectious agents. The invention also relates to a test kit useful in the assay.

BACKGROUND OF THE INVENTION

Detection of nucleic acids has grown in recent years as a means for early detection of genomic features, infectious agents and various organisms which are present in very small quantities in a human or animal test specimen. Detection procedures are normally based on the concept of complementarity whereby two DNA strands are bound together by hydrogen bonds and other forces between complementary nucleotides (which are known as nucleotide pairs).

A DNA molecule is normally quite stable, but the strands can be separated or denatured by certain conditions, such as heating. The denatured strands will reassociate only with another strand having a complementary sequence of nucleotides.

Much research has been carried out to find ways to detect only a few molecules of a DNA. Various procedures are known and have been used for almost a decade to amplify or greatly multiply the number of nucleic acids in a specimen for detection. Such amplification techniques include polymerase chain reaction (PCR), ligase chain reaction (LCR) and others which are less developed.

PCR is the most well known and involves the hybridization of primers to the strands of a target nucleic acid in the presence of a DNA polymerization agent and deoxyribonucleotide triphosphates under appropriate conditions. The result is the formation of primer extension products throughout several cycles and exponential multiplication of the number of original target strands. Further details about PCR can be obtained by consulting U.S. Pat. No. 4,683,195 (Mullis et al), U.S. Pat. No. 4,683,202 (Mullis) and U.S. Pat. No. 4,965,188 (Mullis et al).

While the amplification procedures such as PCR provide opportunities for detection of small amounts of target nucleic acid, they also create a problem with contamination by artificially generated oligonucleotides from one reaction vessel to another. False positive results can be seen as the contaminants are amplified along with the target nucleic acid of the new specimen. This can have serious consequences, especially when infectious agents are being investigated. Both physical containment and chemical "sterilization" techniques are being considered in the industry to reduce such contamination. Physical containment measures have their advantages but also require considerable complexity in engineering and design of the reaction vessels. Chemical sterilization techniques are discussed in the art, but have not yet been successfully demonstrated.

It would be useful to find a way to simplify the amplification process without having to worry about contaminating materials from one reaction vessel to another. It would also be desirable to have an amplification process which can be quantitative in nature. Such processes might be useful in treatment of diseases rather than mere detection thereof.

A homogeneous amplification process considered to be quantitative in nature is described in EP-A-0 487 218 (Tosoh, published May 27, 1992), whereby certain fluorescent dyes are used to bind with double-stranded DNA during or after amplification. The level of change in fluorescent signal upon binding is apparently correlated to the amount of target nucleic acid in the specimen. Classes of fluorescent dyes considered useful in the Tosoh publication are ethidium bromide, acridine orange, bis-benzimidazoles (such as Hoechst 33258), diaminophenylindole, actinomicins, thiazole orange and chromomycins. By "homogeneous" is meant that the process does not require a separation of the detected target nucleic acid from nontargeted materials.

The same type of dyes are also useful for the detection of a DNA polymerase, as described in U.S. Pat. No. 5,049,490 (Sutherland et al).

While the dyes described above (for example, ethidium bromide and the Hoescht dyes) readily bind to DNA, the background evident from their use is often too high for significant sensitivity. Thus, there is a desire to find dyes which bind well to DNA, but which exhibit higher sensitivity and lower background.

Certain bis-intercalating dyes have been described as sensitive dyes for staining amplified nucleic acids, e.g. by Mansfield et al, *BioTechniques* 15 (2), pages 274–279 (1993). While such dyes are useful for staining nucleic acids and overcome the background problems noted above, they bind so tightly to the nucleic acids that they inhibit the amplification process. Thus, they can be used only at the end of amplification, not during such a process.

It would be desirable to have a more sensitive homogeneous assay which can be used in a contained system for quantitative detection of amplified target nucleic acids, thereby avoiding the problem with contaminants. Such an assay should be highly sensitive for low levels of nucleic acids and be easy to manufacture and use. Moreover, it would be desirable to be able to monitor the progress of amplification with an incorporated detection means so that it is present during amplification.

SUMMARY OF THE INVENTION

The problems noted above have been overcome with a homogeneous assay for detection of a double-stranded target nucleic acid, comprising the steps of:

A) amplifying a double-stranded target nucleic acid,

B) contacting the resulting amplified double-stranded target nucleic acid with a fluorescent dye which, when bound to the double-stranded target nucleic acid, exhibits a detectable signal as compared to either: the signal generated when the dye is bound to a single strand of the double-stranded target nucleic acid, or the signal of the dye in its free form, and C) detecting or monitoring the detectable signal as a measure of the presence or amount of the double-stranded target nucleic acid, whereby the fluorescent dye is an unsymmetrical cyanine dye having a binding constant ($K_b$) with double-stranded nucleic acids of from about $1 \times 10^4$ to about $5 \times 10^5$, and is represented by the structure (I):

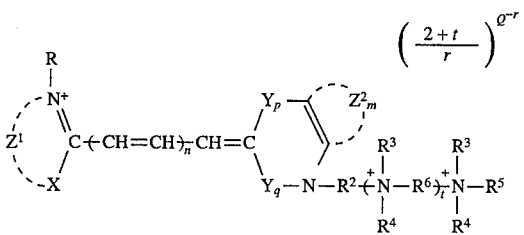

wherein

X is —S—, —O—, —Se—, =CH— or —NR$^1$—,

Y is —CH=CH—,

R is alkyl of 1 to 6 carbon atoms,

R$^1$ is hydrogen or alkyl of 1 to 6 carbon atoms,

R$^2$ and R$^6$ are independently alkylene of 1 to 10 carbon atoms,

R$^3$, R$^4$ and R$^5$ are independently alkyl of 1 to 6 carbon atoms,

Z$^1$ comprises the carbon and hetero atoms necessary to complete a 5- or 6-membered heterocycle which can have up to 3 aromatic carbocyclic or heterocyclic rings fused thereto, Z$^2$ comprises the carbon atoms necessary to complete a 5- or 6-membered aromatic ring which can have up to two aromatic carbocyclic or heterocyclic rings fused thereto, Q is an acid anion, n is 0, 1 or 2, m, p and q are independently 0 or 1, provided that p and q are not the same, r is 1 or 2, and t is 0, 1 or 2, and whereby the detecting or monitoring is carried out without binding the amplified double-stranded target nucleic acid to a capture probe.

This invention also provides a method for monitoring the amplification of a double-stranded target nucleic acid, comprising the steps of:

A) amplifying a double-stranded target nucleic acid in the presence of a fluorescent dye which, when bound to the double-stranded target nucleic acid, exhibits a detectable signal as compared to either: the signal generated when the dye is bound to a single strand of the double-stranded target nucleic acid, or the signal of the dye in its free form, and B) detecting or monitoring the detectable signal as a measure of the presence or amount of the double-stranded target nucleic acid during the amplification step, whereby the fluorescent dye is as described above in the foregoing method, and whereby the detecting or monitoring is carried out without binding the amplified double-stranded target nucleic acid to a capture probe.

Still further, this invention provides a test kit for homogeneous amplification and detection of a double-stranded target nucleic acid, comprising in the same or separate packaging:

1) a fluorescent dye which, when bound to a double-stranded target nucleic acid, exhibits a detectable signal as compared to either: the signal generated when the dye is bound to a single strand of the double-stranded target nucleic acid, or the signal of the dye in its free form, whereby the fluorescent dye is as described above for the methods of this invention, and 2) at least one amplification reagent.

The present invention provides a simpler, highly sensitive homogeneous assay for the detection of a target nucleic acid either during or after amplification. Thus, the method can be used to quantitatively monitor amplification and the amount of nucleic acid at any given point in the procedure. It can also be used to detect the amount of nucleic acid at the end of amplification. Because the method is homogeneous, it can be readily carried out in any suitable containment vessel without the need for separation and capture steps as are common in heterogeneous procedures. Contamination from one vessel to another is avoided since there is no need to remove reagents from the reaction vessel after amplification. Most importantly, the assay is more sensitive than previously reported assays using common fluorescent dyes such as ethidium bromide and Hoescht 3258 dye because background signal is lower.

These advantages are achieved by using a specific class of fluorescent dyes which have a high affinity for the double-stranded nucleic acids being amplified and detected in a specific range. The binding affinity is more than many common fluorescent dyes, but not too great so as to inhibit amplification of the target nucleic acid. The dyes are at least bivalent, that is, having at least two cationic charges per molecule. A more detailed definition of these dyes is provided below.

BRIEF DESCRIPTION OF THE DRAWING

The FIGURE is a graphical plot of fluorescent intensity vs. PCR cycles and is explained in more detail in Example 1 below.

DETAILED DESCRIPTION OF THE INVENTION

The general principles and conditions for amplification and detection of nucleic acids using polymerase chain reaction are quite well known, the details of which are provided in numerous references including U.S. Pat. Nos. 4,683,195, 4,683,202 and 4,965,188 (noted above), all of which are incorporated herein by reference. Thus, in view of the teaching in the art and the specific teaching provided herein, a worker skilled in the art should have no difficulty in practicing the present invention by making the adjustments taught herein to amplify one or more nucleic acids.

Other amplification procedures which can be used in the practice of this invention include ligase chain reaction as described, for example, in EP-A-0 320 308 (published December, 1987) and EP-A-0 439 182 (published January, 1990), self-sustained sequence replication as described, for example, by Birkenmeyer et al, *J.Virol.Meth.* 35, pp. 117–126 (1991), "Gap-LCR" and variations thereof and other procedures which would be readily apparent to one skilled in the art. While the remainder of this disclosure, however, is directed to practicing the invention using PCR, it would be readily apparent to one skilled in molecular biology how the teaching herein could be adapted to the other useful amplification techniques.

The present invention is directed to the amplification or detection of one or more specific nucleic acid sequences present in one or more target nucleic acids in a test specimen. Test specimens can include cellular or viral material, hair, body fluids or other materials containing genetic DNA or RNA which can be detected. While the primary purpose of detection could be diagnostic in nature, the invention could also be used to improve the efficiency of cloning DNA or messenger RNA, or for obtaining large amounts of the desired sequence from a mixture of nucleic acids resulting from chemical synthesis.

Nucleic acids to be amplified can be obtained from various sources including plasmids, and naturally occurring DNA or RNA from any source (such as bacteria, yeast, viruses, plants, higher animals or humans). It may be extracted from various tissues including blood, peripheral blood mononuclear cells (PBMC), other tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or viral infected cells. In addition, nucleic acids associated with cancers are amplifiable and detectable using the present invention.

Bacteria which can be detected include, but are not limited to, bacteria found in human blood, Salmonella species, Chlamydia species, Gonococcal species, Shigella species and Mycobacterium species. Viruses which are detectable include, but are not limited to, herpes simplex viruses, Epstein Barr virus, human cytomegalovirus, human papilloma virus, hepatitis viruses and retroviruses such as HTLV-I, HTLV-II, HIV-I and HIV-II. Protozoan parasites, yeasts and molds are also detectable. Other detectable species would be readily apparent to one skilled in the art.

A "PCR reagent" refers to any of the reagents considered essential to PCR, namely a set of primers for the opposing strands of each target nucleic acid, a DNA polymerase, a DNA polymerase cofactor, and two or more deoxyribonucleoside-5'-triphosphates.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of the other PCR reagents, and suitable temperature and pH.

The primer is preferably single stranded for maximum efficiency in amplification, but may be double stranded if desired. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides, and preferably, they have from 18 to 45 nucleotides.

The primers used in the present invention are selected to be "substantially complementary" to the different strands of the specific sequence to be amplified. This means that they must be sufficiently complementary to hybridize with their respective strands to form the desired hybridized products and then be extendible by a DNA polymerase. In the preferred and most practical situation, the primer has exact complementarity to the target nucleic acid.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). As used herein, the term "primer" also refers to a mixture of primers.

A DNA polymerase is an enzyme which will add deoxynucleoside monophosphate molecules to the 3'-hydroxy end of the primer in a complex of primer and template, but this addition is in a template dependent manner (that is, dependent upon the specific nucleotides in the template). Useful DNA polymerases include for example, *E. coli* DNA polymerase I, T4 DNA polymerase, Klenow polymerase, reverse transcriptase and others known in the art.

The DNA polymerase is preferably "thermostable", meaning that it is generally stable to heat and preferentially active at higher temperatures, especially the high temperatures used for denaturation of DNA strands. More particularly, the thermostable DNA polymerases are not substantially inactivated at the high temperatures used in PCR. Such temperatures will vary depending upon a number of reaction conditions, including pH, salt concentration, and other conditions known in the art.

A number of thermostable DNA polymerases have been reported in the art, including those mentioned in detail in U.S. Pat. No. 4,965,188 (noted above) and U.S. Pat. No, 4,889,818 (issued Dec. 26, 1989 to Gelland et al), incorporated herein by reference. Particularly useful polymerases are those obtained from various Thermus bacterial species. Preferred thermostable enzymes are DNA polymerases obtained from *Thermus aquaticus, Thermus filiformis, Thermus flavus* or *Thermus thermophilus*. Other useful thermostable polymerases are obtained from a variety of other microbial sources including *Thermococcus literalis, Pyrococcus furiosus, Thermotoga* sp. and those described in WO-A-89/06691 (published Jul. 27, 1989). Some useful enzymes are commercially available. A number of techniques are known for isolating naturally-occurring polymerases from organisms, and cloning and other synthetic techniques for preparing polymerases using recombinant techniques, are also known from the art cited above.

A DNA polymerase cofactor refers to a nonprotein compound on which the enzyme depends for activity. A number of such materials are known in the art, including manganese and magnesium compounds which release divalent manganese or magnesium ions in the aqueous reaction mixture. Useful cofactors include, but are not limited to, manganese and magnesium salts, such as chlorides, sulfates, acetates and fatty acid salts. The smaller salts, such as chlorides, sulfates and acetates, are preferred. Magnesium chlorides and sulfates are most preferred.

Also needed for PCR are two or more deoxyribonucleoside-5'-triphosphates, such as two or more of dATP, dCTP, dGTP, dTTP and dUTP. Analogues such as dITP and 7-deaza-dGTP are also useful. Preferably, the four common triphosphates (dATP, dCTP, dGTP and dTTP) are used together in PCR.

The PCR reagents described herein are provided and used in PCR in suitable concentrations to provide amplification of the target nucleic acid.

The minimal amounts of DNA polymerase is generally at least about 0.5 unit/100 µl of solution, with from about 2 to about 25 units/100 µl being preferred, and from about 7 to about 20 units/100 µl being more preferred. Other amounts may be useful for given amplification systems. A "unit" is defined herein as the amount of enzyme activity required to incorporate 10 nmoles of total nucleotides (dNTP's) into an extending nucleic acid chain in 30 minutes at 74° C.

The concentration of each primer is at least about 0.01 μmolar with from about 0.2 to about 1 μmolar being preferred. Other amounts may be useful in certain amplification systems. The primers can be present in the same or different amounts.

The DNA polymerase cofactor is generally present in an amount of from about 0.5 to about 20 mmolar, and each dNTP is generally present at from about 0.1 to about 2 mmolar in the reaction mixture. Other amounts of the cofactor and dNTP's may be useful in certain amplification systems.

The PCR reagents can be supplied individually, or in various combinations, or all in a buffered solution having a pH in the range of from about 7 to about 9, using any suitable buffer, many of which are known in the art. The reaction mixture used for amplification is generally similarly buffered although other pH values may be used in certain amplification systems.

A target nucleic acid can be obtained from any of a variety of sources as noted above. Generally, it must be extracted in some manner to make it available for contact with the primers and other reaction materials. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc. Natl. Acad. Sci. USA*, 78 (9), pp. 5759–5763 (1981), Saiki et al, *Bio/Technology*, 3, pp. 1008–1012 (1985) and U.S. Pat. No. 5,231,015 (Cummins et al).

Since the target nucleic acid to be amplified and detected is usually in double stranded form, the two strands must be separated (that is, denatured) before priming can take place. This can occur during the extraction process, or be a separate step afterwards. Heating to a suitable temperature (identified as "first temperature" herein) is a preferred means for denaturation. Generally, this first temperature is in the range of from about 85° to about 100° C. for up to several minutes, but generally for example from about 1 to about 40 seconds.

The denatured strands are then primed with the appropriate set of primers by cooling the reaction mixture to a second temperature which is generally within the range of from about 55° to about 75° C. Cooling takes place over any suitable time period up to several minutes, but generally cooling is carried out within 60 seconds, and more preferably for from about 5 to about 25 seconds.

Once the denatured strands are cooled, the reaction mixture containing the PCR reagents is incubated at a third temperature for up to several minutes. More generally, incubation is for from 1 to about 80 seconds, and preferably for from 1 to about 40 seconds, to effect formation of primer extension products. Generally, the third temperature is in the range of from about 55° to about 75° C. Preferably, it is in the range of from about 62° to about 68° C.

In a most preferred embodiment, the second and third temperatures are the same and are within the range of from about 62° to about 68° C. Thus, priming and primer extension can be carried out at the same temperature for a suitable time up to several minutes, with a time of from about 5 to about 120 seconds being preferred, and a time of from about 10 to about 90 seconds being more preferred.

After formation of primer extension products, the reaction mixture is heated over a suitable period of time of up to several minutes to denature the primer extension products. Generally, the reaction mixture is heated for from about 5 to about 20 seconds, and maintained at that temperature for from about 1 to about 80 seconds to denature the products. This completes an amplification cycle.

PCR is generally carried out for at least 20 cycles, with 20 to 50 cycles being preferred. Each cycle is generally from about 20 to about 360 seconds, with a cycle time of from about 30 to about 120 seconds being preferred and from about 30 to about 90 seconds being more preferred. Longer cycle times may be useful for certain amplification systems.

While some amplification systems and procedures can be carried out in a discontinuous manner, that is, with cycles having different lengths or with interruptions for adding reagents or taking out samples, the method of this invention is preferably conducted in a continuous, automated manner so that the reaction mixture is temperature cycled in a controlled manner for a desired number of times. A number of instruments have been developed for this purpose, as one of ordinary skill in the art would know.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (noted above). Also described therein are means for heating and cooling the test pack at repeated intervals (that is, through cycles) appropriate for the method of the present invention. Further details regarding useful PCR processing equipment can be obtained from the considerable literature in the field, and would be readily ascertainable by one skilled in the art.

Besides chemical test packs described above, the method can be carried out in other containers such as those described in more detail in U.S. Pat. No. 4,902,624 (Columbus et al), U.S. Pat. No. 4,683,195 (noted above) and any other suitable container which is readily apparent to one skilled in the art. A major advantage of the present invention is that amplification and detection can be carried out in a closed container so as to eliminate contamination. Thus, closed containers which have been designed for that purpose are suitable for practicing the homogeneous method of this invention. Since detection is carried out by measuring emission from a fluorescent dye, the container must be adapted to allow such measurements. Thus, the container can be made of glass, and transmissive polymers which would be readily apparent to one skilled in the art.

As noted above, the fluorescent dye described herein can be used at any time during or after amplification to detect the target nucleic acid. Preferably, the dye is present from the beginning of the method so that the progress of amplification can be monitored throughout. The particular fluorescent dye, when bound to the double-stranded target nucleic acid, exhibits a detectable signal as compared to the signal generated when the dye is bound to a single strand of the target nucleic acid. Alternatively, the signal from the dye bound to the double-stranded target nucleic acid can be compared to the signal provided by the dye in its free form (that is, unbound to either single- or double-stranded nucleic acids). As used herein, the term "detectable signal" refers to any detectable change in signal, such as an increase or decrease in emission intensity, a shift (in either direction) in emission maximum wavelength by at least 5 nm but no shift in the excitation wavelength, a shift (in either direction) in the maximum excitation wavelength but no shift in the emission wavelength, a shift in both maximum excitation and emission wavelengths, or a combination of any of these effects. Preferably, the detectable signal is evidenced by an increase in emission intensity.

The detectable signal is monitored or detected using any suitable fluorescent spectrophotometer for the given excitation and emission wavelengths of a given fluorescent dye. Detectable signal can be monitored at any time in the amplification procedure, that is, after any amplification cycle, or it can be carried out after the last amplification cycle. In the first instance, amplification is actually carried out, at least in some cycles, in the presence of the fluorescent dye.

The fluorescent dyes useful herein are generally defined as unsymmetrical cyanine dyes having a binding constant ($K_b$) within the range of from about $1 \times 10^4$ to about $5 \times 10^5$ (molar$^{-1}$). As used to define $K_b$, "about" refers to a variance of 10%. The dyes are also water-soluble or water-dispersible so they can bind to the nucleic acids in the aqueous reaction mixture. Depending upon the anions used, the dyes may be dissolved in a water-miscible solvent.

Moreover, the dyes useful in this invention are further defined by the parameter "KC" which is calculated using the following formula:

$KC = K_p \times \text{Dye Concentration (C)} \times 2$.

$K_p$ is partition coefficient. As used herein, the useful fluorescent dyes have a "KC" value of about 20 or less, wherein "about" refers to a variance of 10%. The KC values for several useful dyes, as well as several dyes outside the scope of the invention, are provided in Example 3 below.

More particularly, the useful dyes are defined by the structure (I):

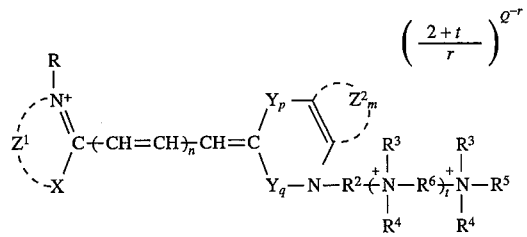

wherein X is —S—, —O—, —Se—, =CH— or —NR$^1$—. Preferably, X is —S— or —O—.

Also in Structure (I), Y is —CH=CH—.

R is substituted or unsubstituted alkyl of 1 to 6 carbon atoms (such as methyl, ethyl, propyl, isopropyl, butyl, tert-butyl, pentyl and hexyl). Preferably, R is substituted or unsubstituted alkyl of 1 to 3 carbon atoms, and more preferably, R is methyl or ethyl. Most preferably, R is methyl.

R$^1$ can be hydrogen or a substituted or unsubstituted alkyl of 1 to 6 carbon atoms, as defined above for R. More preferably, R$^1$ is hydrogen or substituted or unsubstituted alkyl of 1 to 3 carbon atoms as defined above, and most preferably, R$^1$ is hydrogen.

R$^2$ and R$^6$ are independently substituted or unsubstituted alkylene of 1 to 10 carbon atoms (such as methylene, ethylene, trimethylene, isopropylene, n-hexylene, n-pentylene, n-hexylene, n-octylene and n-decylene). Preferably, R$^2$ and R$^6$ are independently substituted or unsubstituted alkylene of 1 to 4 carbon atoms with trimethylene being most preferred.

R$^3$, R$^4$ and R$^5$ are independently substituted or unsubstituted alkyl of 1 to 6 carbon atoms (as defined above for R and R$^1$). Preferably, each of these groups is independently substituted or unsubstituted alkyl of 1 to 3 carbon atoms, and most preferably, each is methyl.

Z$^1$ comprises the carbon and hetero atoms necessary to complete a 5- or 6-membered heterocyclic ring, such as a benzoxazolium, benzothiazolium, benzimidazolium, quinolino[2,3-d]thiazolium, naphtho[2,3-d]thiazolium, naphtho[1,2-d]thiazolium, benzoselenazolium, pyridinium and quinolinium. The heterocyclic ring formed with Z$^1$ can have up to three additional 5- or 6-membered aromatic fused rings (either carbocyclic or heterocyclic) attached thereto. Other ring structures would be readily apparent to one skilled in the art. The benzoxazolium, benzothiazolium and benzimidazolium rings are preferred with the first two rings being more preferred. Such rings can be substituted in various positions with lower alkyl (1 to 3 carbon atoms) or any other substituent which would be readily apparent to one skilled in the art, as long as such substituents do not adversely affect the fluorescent and nucleic acid binding properties upon which this invention is dependent, or undesirably slow down diffusibility of the compound in aqueous systems.

In Structure (I), Z$^2$ comprises the carbon and hetero atoms necessary to complete a 5- or 6-membered aromatic ring which is attached to the illustrated heterocyclic ring, thereby providing a fused ring system. Z$^2$ can have up to two additional aromatic fused rings (carbocyclic or heterocyclic) attached thereto. Preferably, the completed ring is a benzo or naphtho ring, with a benzo ring being most preferred, thereby resulting in a quinoline ring.

Also in the noted Structure (I), n is 0, 1 or 2, and preferably, it is 0 or 1.

Further, m, p and q are independently 0 or 1, provided that p and q are not the same. Preferably, at least one of p and q is 1, and most preferably, p is 0 and q is 1. Also, t is 0, 1 or 2, and is preferably 0.

Q is a suitable acid anion having the appropriate charge. Such anions include, but are not limited to, chloride, bromide, p-toluenesulfonate, methosulfate, sulfate, nitrate and others readily apparent to one skilled in the art. In the structure, r is 1 or 2.

Particularly useful fluorescent dyes are commercially available from Molecular Probes, Inc. having the trade names and $K_p$ values listed in Table I below. However, this invention is not to be construed as limited to the particular Molecular Probes, Inc. dyes listed therein since these are but preferred dyes. The cations of these preferred dyes are also identified below by chemical structure. The compounds can include any suitable divalent anion, or two monovalent anions. Iodide is preferred.

COMPOUND A:
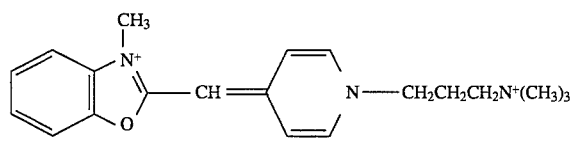
COMPOUND B:
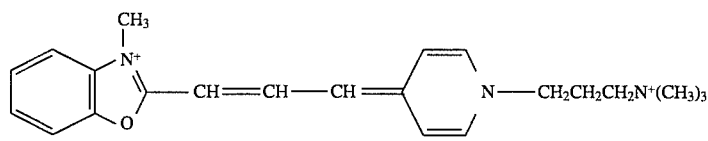
COMPOUND C:
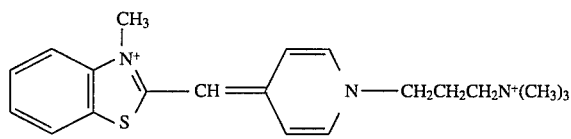
COMPOUND D:
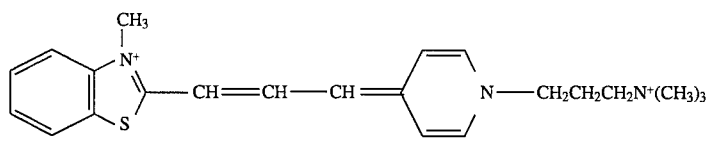
COMPOUND E:
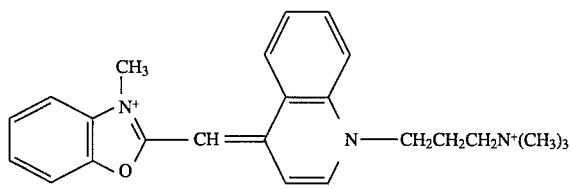
COMPOUND F:
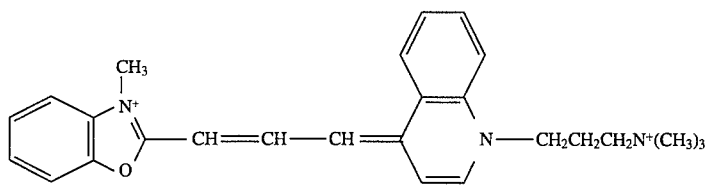
COMPOUND G:
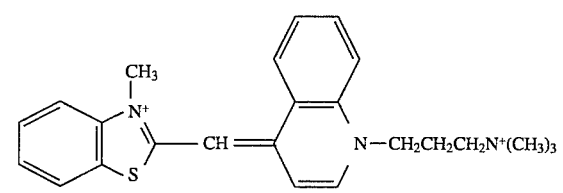
COMPOUND H:
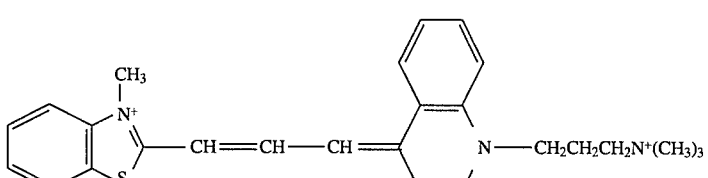

TABLE I

| Compound | Tradename | $K_b$* |
|---|---|---|
| A | PO-PRO-1 | $3.6 \times 10^4$ |
| B | PO-PRO-3 | NA** |
| C | BO-PRO-1 | $5.8 \times 10^4$ |
| D | BO-PRO-3 | $8.7 \times 10^4$ |
| E | YO-PRO-1 | $1.5 \times 10^5$ |
| F | YO-PRO-3 | $6 \times 10^4$ |
| G | TO-PRO-1 | $3.6 \times 10^5$ |
| H | TO-PRO-3 | $1.1 \times 10^5$ |

**NA = not available

*The $K_b$ values in the table were calculated by dividing the partition coefficient (Kp) reported in the Molecular Probes, Inc. catalog, page 224, by 55, the molarity of water.

The amount of fluorescent dye used in the practice of the invention will vary with the particular dye because of varying binding constants and emission intensities and the amount of target nucleic acid suspected of being present. However, in general, the amount is at least about $10^{-9}$ molar, and preferably, it is from about $10^{-8}$ to about $10^{-5}$ molar. A practical upper limit is about $10^{-5}$ molar but the invention is not to be construed as limited thereto. As used in this paragraph, "about" is meant to refer to a variance of 10%. The dyes may be supplied in an aqueous solution containing minor amounts of water-miscible organic solvents, such as dimethyl sulfoxide.

Contact of fluorescent dye and amplified target nucleic acid can be carried out at any suitable temperature, but preferably, it is at room temperature. The reaction between dye and nucleic acid may take from several minutes up to several hours to complete, but longer or shorter times may be useful in certain assays.

The following examples are included to illustrate the practice of this invention, and are not meant to be limiting in any way. All percentages are by weight unless otherwise noted.

Materials and Methods for Examples:

The primers used in Examples 1 and 2 had the following sequences which are complementary to the gag region of HIV-I DNA:

SEQ ID NO:1: 5'-X-ATAATCCACC TATCCCAGTA GGAGAAAT-3'

SEQ ID NO:2: 5'-X-TTTGGTCCTT GTCTTATGTC CAGAATGC- 3'.

The primers used in Example 3 had the following sequences which are complementary to the gag region of HIV-I DNA:

SEQ ID NO:3: 5'-X-AGTGGGGGGA CATCAAGCAG CCATGCAA-3'

SEQ ID NO:4: 5'-X-CCTGCTATGT CACTTCCCCT TGGTTCTCTC-3'

In the primers, X represents a biotinyl moiety appended to the oligonucleotide through two aminotetraethylene glycol spacer groups using the technology described in U.S. Pat. No. 4,962,029 (Levenson et al).

The capture probe used in the assays of Example 1 and 2, and Example 3, respectively, had the following sequences:

SEQ ID NO:5: 5'-ATCCTGGGAT TAAATAAAAT AGTAAGAATG TATAGCCCTA C-3

SEQ ID NO:6: 5'-GAGACCATCA ATGAGGAAGC TGCAGAAT-3'.

These probes were covalently attached to polymeric particles (1 μm average diameter) prepared, using conventional emulsion polymerization techniques, from poly[styrene-co-3-(p-vinylbenzylthio)propionic acid] (95:5 weight percent, 1 μm average diameter). A suspension of the particles in water was washed with 2-(N-morpholino)ethanesulfonic acid buffer (0.1 molar, pH 6), and suspended to about 10% solids. A sample (3.3 ml) of the washed particles, diluted to 3.33% solids in the buffer (0.1 molar, was mixed with 1-(3 -dimethylaminopropyl)-3-ethylcarbodiimide hydrochloride (2.1 ml of 84 mg/ml water) and the probe (983 μl of 44.44 OD/ml nanopure water). The resulting suspension was heated at 50° C. in a water bath for about two hours with intermittent mixing and centrifuged. The particles were then washed three times with tris(hydroxymethyl)aminomethane buffer (0.01 molar, pH 8) containing (ethylenedinitrilo)tetraacetic acid disodium salt (0.0001 molar) and resuspended therein to 4% solids. The final saturation of probe on the particles was about 75%.

Upon dilution to 2% solids, the capture reagents were mixed with a polymeric adhesive (0.2%) formed from poly[methyl acrylate-co-sodium 2 -acrylamido-2-methyl-propane sulfonic acid-co-2-acetoacetoxyethyl methacrylate] (90:4:6 weight percent) in buffer and deposited in the pouches described in Example 2.

Recombinant DNA polymerase from *Thermus aquaticus* was obtained using conventional procedures.

YO-PRO-1, YOYO-1, BO-PRO-1, TO-PRO-1, TO-PRO-3, TOTO-1 and TOTO-3 fluorescent dyes, in 10% dimethyl sulfoxide, were obtained from Molecular Probes, Inc.

Glycerol and tris(hydroxymethyl)aminomethane buffer were obtained from Sigma Chemical.

HIV-I target DNA was obtained from HUT78/HIV AAV cells obtained from Bernie Poiesz of Syracuse University. Each cell contained about 1 HIV-I copy.

The leuco dye dispersion used in Example 2 contained agarose (0.5%), 4,5-bis(4-dimethylaminophenyl)-2-(4-hydroxy-3-methoxyphenyl)imidazole leuco dye (250 μmolar), diethylenetriaminepentaacetic acid (100 μmolar), 4-hydroxyacetanilide (5 mmolar), polyvinyl pyrrolidone (112 mmolar) and sodium phosphate, monobasic, 1-hydrate (10 mmolar).

The conjugate solution used in Example 2 contained a conjugate (126 μl/l, 1.25 g total protein) of streptavidin and horseradish peroxidase obtained from commercial sources (Zymed Laboratories, Inc., 2:1 enzyme to streptavidin ratio), casein (0.5%) and merthiolate (0.5%) in 3-(4-morpholino)propanesulfonic acid buffer (0.1 molar).

The wash solution used in Example 2 contained sodium chloride (373 mmolar), (ethylenedinitrilo)tetraacetic acid disodium salt (2.5 mmolar), decyl sodium sulfate (38 mmolar) and ethylmercurithiosalicylic acid, sodium salt (25 μmolar) in sodium phosphate, monobasic 1-hydrate buffer (25 mmolar, pH 7.4).

The remainder of the reagents and materials were obtained using commercial sources or prepared at Eastman Kodak Company using conventional procedures.

EXAMPLE 1

Detection of Amplified HIV-I DNA

This example demonstrates the present invention to detect HIV-I DNA which has been amplified by PCR.

The final PCR reaction mixture contained the primers SEQ ID NO:1 and SEQ ID NO:2 (0.4 μmolar of each), magnesium chloride (10 mmolar), each of dATP, dCTP, dGTP and dTTP (1.5 mmolar of each), tris(hydroxymethyl)aminomethane buffer (10 mmolar, pH 8), ethylenediaminetetraacetic acid (0.1 mmolar), potassium chloride (50 mmolar), DNA polymerase (160 units/ml) and Kodak Ultrapure Human DNA (0.22 μg/μl), glycerol (7.5%).

The YO-PRO-1 dye (10 μmolar), Compound E identified above, was prepared from a stock solution in dimethyl sulfoxide (1 mmolar) by dilution with tris(hydroxymethyl)aminomethane hydrochloride (10 mmolar) and ethylenediaminetetraacetic acid (1 mmolar) buffer solution. The

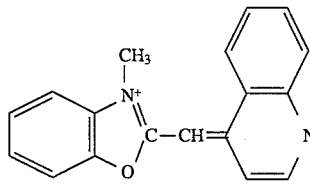

buffered solution was added to the reaction mix to provide a dye concentration of 1 μmolar.

Amplification by PCR of samples (200 μl) of the target HIV-I DNA (10 copies/μl) was carried out in microfuge tubes (0.5 ml) using a Ericomp thermal cycler and the following PCR protocol:

1) Preheat to denature at 95° C. for 15 seconds,
2) each cycle of:
   priming and extension for 40 seconds at 63.5° C, and
   denaturation for 15 seconds at 95° C, and
3) final denaturation for 60 seconds at 5° C.

All reagents, except the DNA polymerase, were mixed with the buffer solution noted above. The resulting mixture was aliquoted into two microfuge tubes (1672 μl/tube). Buffer solution (220 μl) was added to one tube (Sample A) which did not contain fluorescent dye. The YO-PRO-1 dye stock solution (220 μl) was added to the second tube (Sample B). The DNA polymerase (88 μl) and target nucleic acid (220 μl) were then added to each sample. The contents of each sample were split into 10 aliquots of 200 μl each, put into separate microfuge tubes and subjected to PCR as described above. After each of 0, 5, 10, 15, 20, 25, 30, 40 and 45 cycles, a tube was opened. The fluorescence of the contents of that tube was then measured following dilution (100 μl of reaction mixture with 3900 μl of dye solution at a concentration of 1 molar, giving a final fluid volume of 4 ml in the fluorimeter cuvette) on a commercially available Perkin-Elmer LS-5B spectrofluorimeter (excitation at 491 nm, emission at 509 nm).

The results of these measurements are shown in the FIGURE which is a plot of fluorescence intensity vs. the number of PCR cycles. Curve 1 represents the results for Sample A in which no dye was present at the beginning, but to which dye was added when samples were removed after specific numbers of PCR cycles. Curve 2 represents the results for Sample B in which dye was present throughout the entire amplification procedure.

It can be seen that the presence of the YO-PRO-1 dye did not adversely affect PCR even when it was present throughout the entire amplification procedure. Background fluorescence was fairly constant at a level of about 7 to 9 fluorescence units until the 30th PCR cycle, at which point the fluorescence began increasing until it reached about 20 fluorescent units after 45 PCR cycles. This is clearly distinguishable from the initial background signal.

EXAMPLE 2

Comparative Example

The method of this invention was compared to an amplification and detection method outside the scope of this invention, which was carried out using YOYO-1 (1 μmolar final concentration), a tetravalent fluorescent dye, in the buffered solution described above. This dye has the following structure:

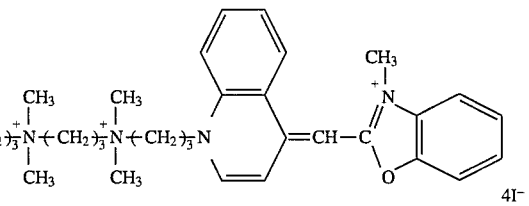

Amplification was carried out using self-contained chemical pouches such as those described in U.S. Pat. No. 5,229,297 (Schnipelsky et al). Those pouches contained the capture probe SEQ ID NO:5 attached to particles which were immobilized in a detection channel where reactions can take place.

The pouches were loaded with reagents, as follows:

The PCR reaction mixture of Example 1 (except the DNA polymerase) was made to a volume of 5472 μl. The resulting mixture was aliquoted into tubes A, B and C (1824 μl each) representing Samples A, B and C, respectively.

The sample in Tube A was diluted with buffer (220 μl) and subjected to amplification without any fluorescence dye present. The dye was added at the end of amplification for quantitative detection of the resulting products.

In addition to the PCR reagents, the sample in Tube B contained YOYO-1 fluorescent dye (0.1 μmolar) which had been added prior to amplification (220 μl of a 10 μmolar solution).

The sample in Tube C also contained YO-PRO-1 fluorescent dye (0.1 μmolar) which had been added prior to amplification (220 μl of a 10 μmolar solution).

The DNA polymerase (88 μl) and target HIV-I DNA target nucleic acid (220 μl) were then added to each tube, and the contents of the each of the three tubes were used to fill the PCR reagent compartment of eight pouches.

Amplification was carried out using the same procedures as in Example 1. The PCR protocol was similarly carried out for 40 cycles using a thermal cycler as follows:

1) Preheat to denature at 95° C. for 60 seconds,
2) each cycle of:
   priming and extension for 40 seconds at 63.5° C., and
   denaturation for 10 seconds at 95° C., and
3) final denaturation for 60 seconds at 95° C.

The results of amplification were detected in three ways: (1) color dye scores visually evaluated as 0 (no signal) to 10 (highest signal density), (2) ethidium bromide stained electrophoretic gels, and (3) fluorescence measured on a commercially available Perkin Elmer fluorimeter.

The noted color scores were obtained by using immobilized capture probes in the pouches with which the amplified target hybridized during incubation for 5 minutes at 42° C. The immobilized target was contacted with the conjugate solution (identified above) for 1 minute at 30° C., followed by the wash solution for 1 minute at 55° C. The leuco dye solution was then added at 30° C. and the resulting color signal was observed after two minutes incubation at 30° C.

Electrophoresis was carried out using commercially available NuSieve 1.5%/Seakem Agarose 1% gels (modified to 2.5% agarose) and ethidium bromide stain. The samples were applied to the gels in conventional TBE buffer (4 μl/100 μl).

Three replicate assays of each sample (A, B and C) were carried out using each detection means. The average result for each detection means was as follows:

| Color Scores from Leuco Dye: | |
|---|---|
| Sample | Average Color Score |
| A | 5.3 |
| B | 0 |
| C | 6 |

These results indicate that amplification was not adversely affected by the presence of the YO-PRO-1 dye in Sample C. However, the presence of the YOYO-1 dye in Sample B inhibited amplification. Sample A was used as a positive control.

| Electrophoretic Results: | |
|---|---|
| Sample | Positive/negative Gel Bands |
| A | 4 Positives out of 4 bands |
| B | 5 Negatives out of 5 bands |
| C | 5 Positives out of 5 bands |

These results are consistent with the color scores noted above. Again, Sample A was used as a positive control. The YOYO-1 dye used in Sample B stopped amplification whereas the YO-PRO-1 dye in Sample C allowed amplification to proceed.

Fluorescent signal was generated using a Perkin-Elmer LS-5B fluorimeter, at the following wavelengths for both dyes:

Excitation: 491 nm,

Emission: 509 nm.

Each amplification product mixture was diluted 100× into a solution of each dye (1 μmolar final concentration). Background signals were obtained from a mixture of amplification reagent mixture and each dye. The results are shown below.

| Fluorescent Results: | |
|---|---|
| Sample | Fluorescent Units |
| Background (YOYO-1) | 0.09 |
| Background (YO-PRO-1) | 0.03 |
| Sample A* | 3.6, 3.7, 3.4, 3.0 |
| Sample A** | 7.1, 6.6, 6.0, 6.0 |
| Sample B | 1.5, 1.5, 1.5, 1.4, 1.4 |
| Sample C | 3.7, 3.5, 3.6, 3.2, 2.8 |

*YO-PRO-1 added after amplification
**YOYO-1 added after amplification

These results indicate that while YOYO-1 provides high nucleic acid staining, it cannot be used during amplification because it considerably inhibits the amplification process. YO-PRO-1 gives a lower overall signal, but it can be included in the reagent mixture during amplification.

Other amplification and detection experiments were conducted whereby the amplification protocol identified above was modified by: (a) using 60 cycles, (b) increasing the denaturation time in each cycle to 20 seconds, or (c) increasing the priming/extension step to 60 seconds. Of these protocol changes, only (a) appeared to make any measurable difference in the presence of YOYO-1. That difference was small and was detectable by fluorescence, but not by gel electrophoresis or color signals.

EXAMPLE 3

Further Comparisons of Fluorescent Dyes

Amplification experiments like those of Example 2 were also carried out to evaluate the usefulness of several other conventional fluorescent dye stains.

In these assays, primers identified above as SEQ ID NO:3 and SEQ ID NO:4 were used, as well as the probe identified as SEQ ID NO:6. Color scores were generated to confirm that amplification did or did not occur in a given experiment. Fluorescence was determined as described in Example 2 except that all amplified samples were mixed with a solution of YOYO-1 (0.1 μmolar) to provide a common minimum threshold of signal.

Fluorescent dyes which were found to be useful in the practice of this invention were YO-PRO-1 (Compound E), BO-PRO-1 (Compound C), TO-PRO-1 (Compound G) and TO-PRO-3 (Compound H). Dyes which were not useful because they generally inhibited PCR were YOYO-1 (identified above) and those identified as follows:

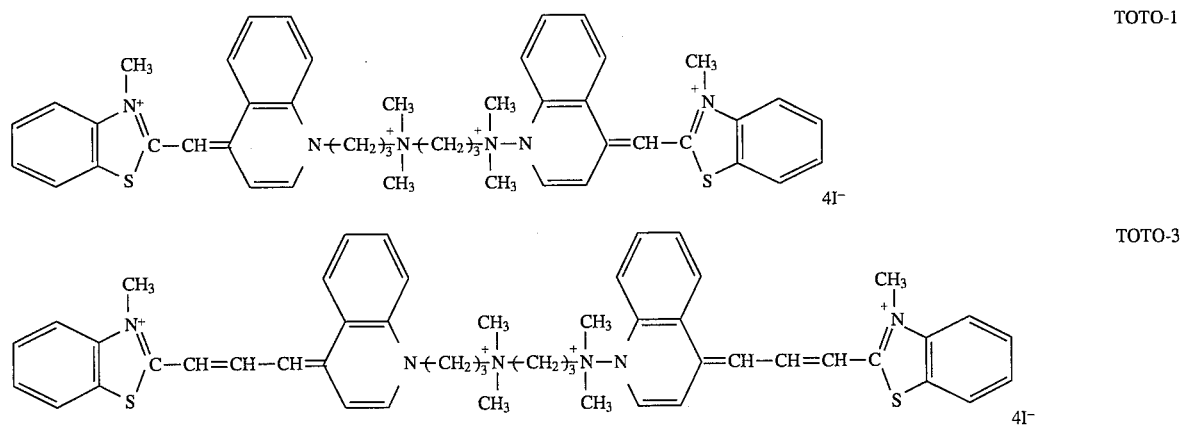

The following Table II lists the fluorescence signal and "KC" values for the dyes tested in the experiments of this example. It is apparent that those dyes having a "KC" value of 20 or less provided acceptable fluorescent signal.

TABLE II

| Dye | Fluorescent Signal | "KC" Value |
|---|---|---|
| BO-PRO-1 | 19.6 | 3.2 |
| TO-PRO-3 | 15.5 | 6.2 |
| YO-PRO-1 | 16 | 8.2 |
| TO-PRO-1 | 8.32 | 20 |
| TOTO-3 | 8.45* | 25 |
| YOYO-1 | 2.18 | 60 |
| TOTO-1 | 2.70 | 110 |

*TOTO-3 provided high fluorescent signal in one experiment, but it was difficult to obtain a repeatable result, whereas the results from the other dyes were repeatable. Thus, confidence in the noted value for TOTO-3 is low.

The invention has been described in detail with particular reference to preferred embodiments thereof, but it will be understood that variations and modifications can be effected within the spirit and scope of the invention.

We claim:

1. A homogeneous method for the detection of a double-stranded target nucleic acid, comprising the steps of:

A) amplifying a double-stranded target nucleic acid,

B) contacting the resulting amplified double-stranded target nucleic acid with a fluorescent dye which, when bound to said double-stranded target nucleic acid, exhibits a detectable signal as compared to either: the signal generated when said dye is bound to a single strand of said double-stranded target nucleic acid, or the signal of the dye in its free form, and C) detecting or monitoring said detectable signal as a measure of the presence or amount of said double-stranded target nucleic acid, whereby said fluorescent dye is an unsymmetrical cyanine dye having a binding constant ($K_b$) with double-stranded nucleic acids of from about $1\times10^4$ to about $5\times10^5$ (molar$^{-1}$) and having a KC value of 20 or less, and is represented by the structure (I):

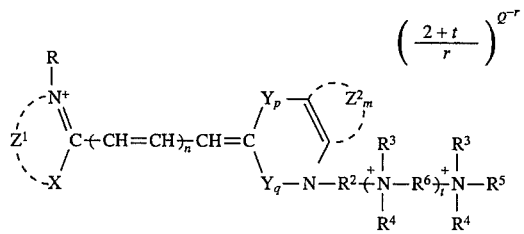

wherein

X is —S—, —O—, —Se—, =CH— or —NR$^{-1}$,

Y is —CH=CH—,

R is alkyl of 1 to 6 carbon atoms,

R$^1$ is hydrogen or alkyl of 1 to 6 carbon atoms,

R$^2$ and R$^6$ are independently alkylene of 1 to 10 carbon atoms,

R$^3$, R$^4$ and R$^5$ are independently alkyl of 1 to 6 carbon atoms,

Z$^1$ comprises the carbon and hetero atoms necessary to complete a 5- or 6- membered heterocyclic ring, Z$^2$ comprises the carbon and hetero atoms necessary to complete a 5- or 6- membered aromatic ring, Q is an acid anion, n is 0, 1, or 2, m, p and q are independently 0 or 1, provided that p and q are not the same, r is 1 or 2, and t is 0, 1 or 2, whereby said detecting or monitoring is carried out without hybridization of said amplified double-stranded target nucleic acid to a capture probe.

2. The method of claim 1 wherein X is —S— or —O—, R is alkyl of 1 to 3 carbon atoms, R$^1$ is hydrogen or alkyl of 1 to 3 carbon atoms, R$^2$ is alkylene of 1 to 4 carbon atoms, R$^3$, R$^4$ and R$^5$ are independently alkyl of 1 to 3 carbon atoms, Z$^1$ comprises the carbon atoms necessary to complete a benzoxazolium or benzothiazolium ring, Z$^2$ comprises the carbon atoms necessary to complete a benzo ring, n is 0 or 1, t is 0 or 1, and at least one but not both of p and q are 1.

3. The method of claim 2 wherein R is methyl or ethyl, R$^2$ is an alkylene of 3 carbon atoms, each of R$^3$, R$^4$ and R$^5$ is methyl, p is 0, q is 1, and t is 0.

4. The method of claim 1 wherein said fluorescent dye is Compound G or H.

5. The method of claim 1 wherein said amplification step A) is carried out using polymerase chain reaction.

6. A method for monitoring the amplification of a double-stranded target nucleic acid, comprising the steps of:

A) amplifying a double-stranded target nucleic acid in the presence of a fluorescent dye which, when bound to said double-stranded target nucleic acid, exhibits a detectable signal as compared to either: the signal generated when said dye is bound to a single strand of said double-stranded target nucleic acid, or the signal of the dye in its free form, and B) detecting or monitoring said detectable signal as a measure of the presence or amount of said double-stranded target nucleic acid during said amplification step, whereby said fluorescent dye is an unsymmetrical cyanine dye having a binding constant ($K_b$) with double-stranded nucleic acids of from about $1\times10^4$ to about $5\times10^5$ (molar$^{-1}$) and having a KC value of 20 or less, and is represented by the structure (I):

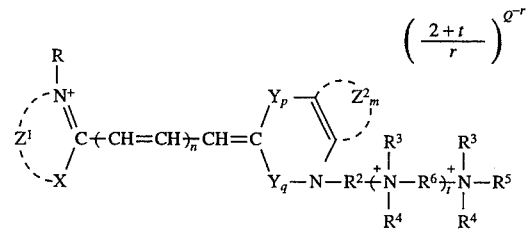

wherein

X is —S—, —O—, —Se—, =CH— or —NR$^1$—,

Y is —CH=CH—,

R is alkyl of 1 to 6 carbon atoms,

R$^1$ is hydrogen or alkyl of 1 to 6 carbon atoms,

R$^2$ and R$^6$ are independently alkylene of 1 to 10 carbon atoms,

R$^3$, R$^4$ and R$^5$ are independently alkyl of 1 to 6 carbon atoms, $Z^1$ comprises the carbon and hetero atoms necessary to complete a 5- or 6- membered heterocyclic ring, $Z^2$ comprises the carbon and hetero atoms necessary to complete a 5- or 6- membered aromatic ring, Q is an acid anion, n is 0, 1, or 2, m, p and q are independently 0 or 1, provided that p and q are not the same, r is 1 or 2, and t is 0, 1 or 2, and whereby said detecting or monitoring is carried out without binding of said amplified double-stranded target nucleic acid to a capture probe.

7. The method of claim 6 wherein X is —S— or —O—, R is alkyl of 1 to 3 carbon atoms, $R^1$ is hydrogen or alkyl of 1 to 3 carbon atoms, $R^2$ is alkylene of 1 to 4 carbon atoms, $R^3$, $R^4$ and $R^5$ are independently alkyl of 1 to 3 carbon atoms, $Z^1$ comprises the carbon atoms necessary to complete a benzoxazolium or benzothiazolium ring, $Z^2$ comprises the carbon atoms necessary to complete a benzo ring, n is 0 or 1, t is 0 or 1, and at least one but not both of p and q are 1.

8. The method of claim 7 wherein R is methyl or ethyl, $R^2$ is an alkylene of 3 carbon atoms, each of $R^3$, $R^4$ and $R^5$ is methyl, p is 0, q is 1, and t is 0.

9. The method of claim 6 wherein said fluorescent dye is Compound G or H.

10. The method of claim 6 wherein said amplification step A) is carried out using polymerase chain reaction.

11. The method of claim 6 wherein said fluorescent dye is present at a concentration of at least about $10^{-9}$ molar.

12. The method of claim 6 wherein said detectable signal is an increase in emission intensity.

13. A test kit for homogeneous amplification and detection of a double-stranded target nucleic acid, comprising in the same or separate packaging:

1) a fluorescent dye which, when bound to a double-stranded target nucleic acid, exhibits a detectable signal as compared to either: the signal generated when said dye is bound to a single strand of said double-stranded target nucleic acid, or the signal of the dye in its free form, whereby said fluorescent dye is an unsymmetrical cyanine dye having a binding constant ($K_b$) with double-stranded nucleic acids of from about $1 \times 10^4$ to about $5 \times 10^5$ (molar$^{-1}$) and having a KC value of 20 or less, and is represented by the structure (I):

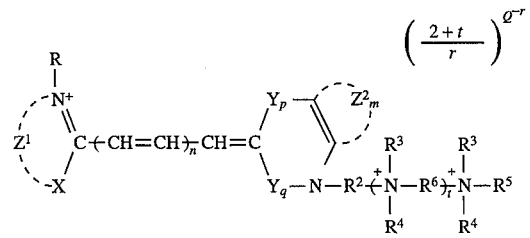

wherein

X is —S—, —O—, —Se—, =CH— or —$NR^1$—,

Y is —CH=CH—,

R is alkyl of 1 to 6 carbon atoms, $R^1$ is hydrogen or alkyl of 1 to 6 carbon atoms, $R^2$ and $R^6$ are independently alkylene of 1 to 10 carbon atoms, $R^3$, $R^4$ and $R^5$ are independently alkyl of 1 to 6 carbon atoms, $Z^1$ comprises the carbon and hetero atoms necessary to complete a 5- or 6- membered heterocyclic ring, $Z^2$ comprises the carbon and hetero atoms necessary to complete a 5- or 6- membered aromatic ring, Q is an acid anion, n is 0, 1, or 2, m, p and q are independently 0 or 1, provided that p and q are not the same, r is 1 or 2, and t is 0, 1 or 2, and 2) at least one PCR reagent, wherein said PRC reagent and said fluorescent dye are in the same package.

14. The test kit of claim 13 wherein said PCR reagent is a primer for the target nucleic acid, a thermostable DNA polymerase, a dNTP or a DNA polymerase cofactor.

15. The test kit of claim 14 wherein all of said PCR reagents are in the same buffered reaction mixture.

16. The test kit of claim 14 further containing a reaction vessel for carrying out amplification and detection of the target nucleic acid.

17. The test kit of claim 14 wherein X is —S—or —O—, R is alkyl of 1 to 3 carbon atoms, $R^1$ is hydrogen or alkyl of 1 to 3 carbon atoms, $R^2$ is alkylene of 1 to 4 carbon atoms, $R^3$, $R^4$ and $R^5$ are independently alkyl of 1 to 3 carbon atoms, $Z^1$ comprises the carbon atoms necessary to complete a benzoxazolium or benzothiazolium ring, $Z^2$ comprises the carbon atoms necessary to complete a benzo ring, n is 0 or 1, t is 0 or 1, and at least one but not both of p and q are 1.

18. The test kit of claim 17 wherein R is methyl or ethyl, $R^2$ is an alkylene of 3 carbon atoms, each of $R^3$, $R^4$ and $R^5$ is methyl, p is 0, q is 1, and t is 0.

19. The test kit of claim 14 wherein said fluorescent dye is Compound G or H.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 28 Nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 1:

ATAATCCACC TATCCCAGTA GGAGAAAT    28

( 2 ) INFORMATION FOR SEQ ID NO:2:

( i ) SEQUENCE CHARACTERISTICS:
        ( A ) LENGTH: 28 Nucleotides
        ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 2:

TTTGGTCCTT GTCTTATGTC CAGAATGC    28

( 2 ) INFORMATION FOR SEQ ID NO:3:

( i ) SEQUENCE CHARACTERISTICS:
        ( A ) LENGTH: 28 Nucleotides ( B ) TYPE: Nucleic acid
        ( C ) STRANDEDNESS: Single
        ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO: 3:

AGTGGGGGGA CATCAAGCAG CCATGCAA 28

( 2 ) INFORMATION FOR SEQ ID NO:4:

( i ) SEQUENCE CHARACTERISTICS:
            ( A ) LENGTH: 30 Nucleotides
            ( B ) TYPE: Nucleic acid
            ( C ) STRANDEDNESS: Single
            ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO: 4:

CCTGCTATGT CACTTCCCCT TGGTTCTCTC 30

( 2 ) INFORMATION FOR SEQ ID NO:5:

( i ) SEQUENCE CHARACTERISTICS:
            ( A ) LENGTH: 41 Nucleotides
            ( B ) TYPE: Nucleic acid
            ( C ) STRANDEDNESS: Single
            ( D ) TOPOLOGY: Linear ( i i ) MOLECULE TYPE: Probe for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 5:

ATCCTGGGAT TAAATAAAAT AGTAAGAATG TATAGCCCTA C 41

( 2 ) INFORMATION FOR SEQ ID NO:6:

( i ) SEQUENCE CHARACTERISTICS:
            ( A ) LENGTH: 28 Nucleotides
            ( B ) TYPE: Nucleic acid
            ( C ) STRANDEDNESS: Single
            ( D ) TOPOLOGY: Linear ( i i ) MOLECULE TYPE: Probe for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Unknown ( x i ) SEQUENCE DESCRIPTION: SEQ ID NO: 6:

GAGACCATCA ATGAGGAAGC TGCAGAAT 2 8